(12) United States Patent
Cavazza et al.

(10) Patent No.: US 6,214,884 B1
(45) Date of Patent: Apr. 10, 2001

(54) COMPOSITION COMPRISING KETANSERIN AND L-CARNITINE OR AN ALKANOYL L-CARNITINE FOR THE TREATMENT OF CRPS

(75) Inventors: Claudio Cavazza; Menotti Calvani, both of Rome (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 09/458,966

(22) Filed: Dec. 10, 1999

Related U.S. Application Data

(63) Continuation of application No. PCT/IT99/00084, filed on Apr. 8, 1999.

(30) Foreign Application Priority Data

Apr. 10, 1998 (IT) .............................................. MI98A0774

(51) Int. Cl.[7] ........................ A61K 31/14; A61K 31/205; A61K 31/505
(52) U.S. Cl. ........................... 514/642; 514/259; 514/556
(58) Field of Search .................................. 514/642, 259, 514/556

(56) References Cited

U.S. PATENT DOCUMENTS 5,973,004 * 10/1999 Howard ................................ 514/561

OTHER PUBLICATIONS

Moesker Pain Clinic (1998) pp. 261–274 XP002119433 Treatment of hyperpathia/allodinia in CRPS earlier called RSDS, a metabolic approach.
Kingery Pain (1997) (2) pp. 123–139 XP002119434 A critical review of controlled clinical trials for peripheral neuropathic pain and complex regional pain syndromes.
Moesker The Pain Clinic, vol. 8, No. 1, 1995, pp. 31–37 XP002119435 The purpose of a Serotonin Antagonist in Reflex Sympathetic Dystrophy.
Dangel Medical Science Monitor, (1997) 3/Suppl. 1 (111–116) XP002119436 Regional analgesia in children with reflex sympathetic dystrophy.

* cited by examiner

Primary Examiner—Theodore J. Criares
Assistant Examiner—Jennifer Kim
(74) Attorney, Agent, or Firm—Nixon & Vanderhye

(57) ABSTRACT

This invention relates to L-carnitine and lower alkanoyl L-carnitines in combination with ketanserin, for the therapeutic treatment of Chronic Regional Pain Syndrome (CRPS).

12 Claims, 2 Drawing Sheets

CRPS: Symptomatology

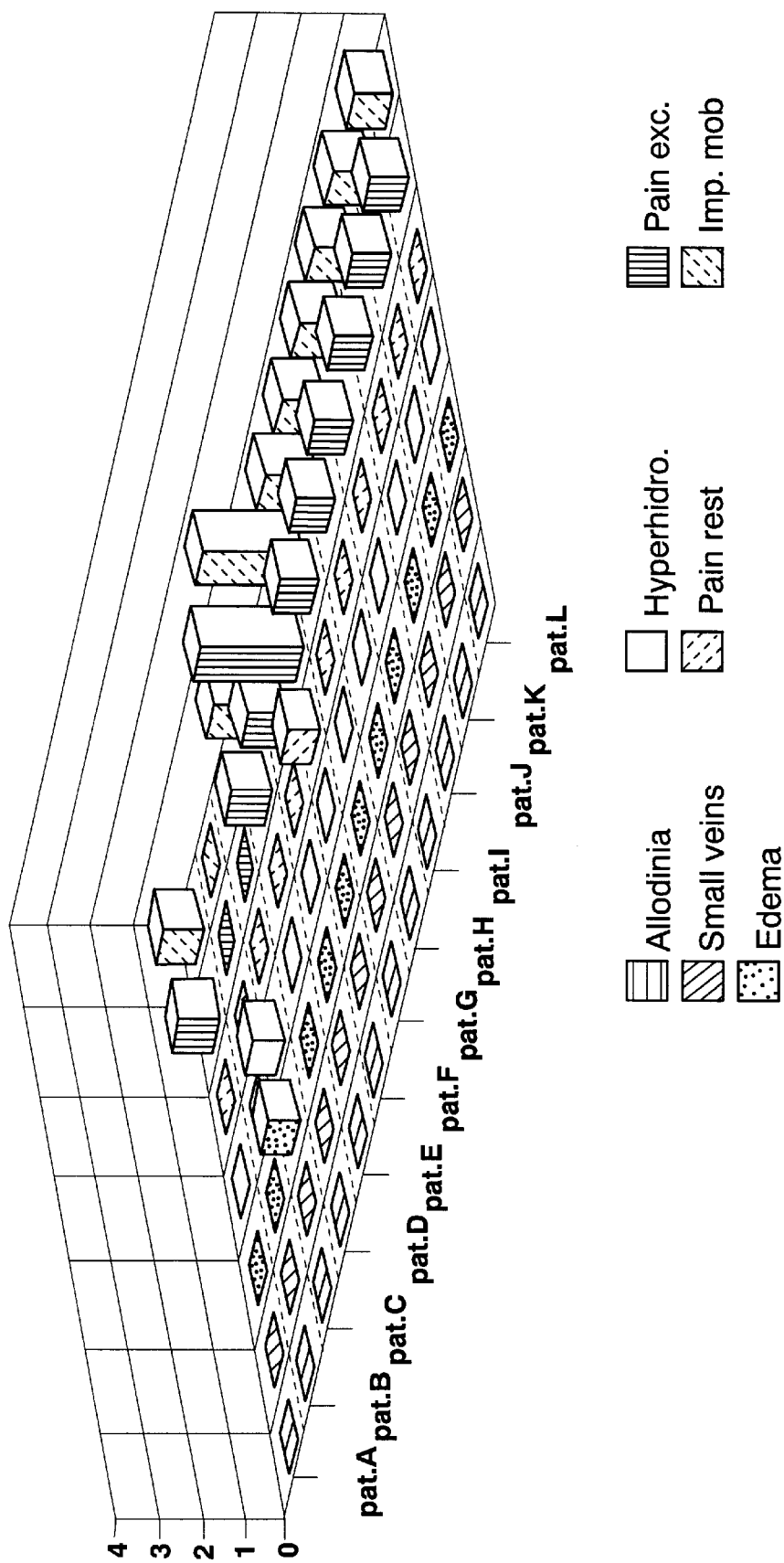
FIG. 2  CRPS: Symptomatology after 3 month

COMPOSITION COMPRISING KETANSERIN AND L-CARNITINE OR AN ALKANOYL L-CARNITINE FOR THE TREATMENT OF CRPS

This is a continuation of PCT application PCT/IT9900084, filed 8 Apr.1999, the entire content of which is hereby incorporated by reference in this application.

Pharmaceutical composition for the treatment of Chronic Regional Pain Syndrome

The present invention relates to L-carnitine and lower alkanoyl L-carnitines or the pharmacologically acceptable salts thereof in combination with ketanserin, for the therapeutic treatment of Chronic Regional Pain Syndrome (CRPS).

CRPS is a pain syndrome, which affects several subjects after a trauma, even a mild entity trauma.

To CRPS are associated disturbs of blood circulation with ischemia and pain, wherein, ischemia gives pain and pain causes ischemia.

Other important symptoms shown by patients affected by CRPS are hyperpathia and allodinia.

CRPS origin is still not clear; for several years it has been considered that the sympathetic nervous system is involved.

For this reason the most effective therapy was effected by blocking the sympathetic innervation with phenol, thermolesion or treating with guanethidine.

The circulation restoration with ketanserin, a serotonine antagonist, constituted an improvement in the treatment of such disease.

With this drug it is possible to treat most of symptoms, but not those caused by hyperpathia and allodinia [A. Moesker et al., in Konservative Therapie Arterieller Durchblutungsstoerungen, Georg Thieme Verlag (Stuttgart, New York), 148–152, 1986; A. Moesker et al., The pain Clinic vol. 8,n°.1, 31–37 (1995); A. Moesker et al., ibid.vol 12, 269–302 (1991)].

More recently, following to the identification of the oxygen free radical during CRPS, dimethyl sulfoxide has been utilised (R. J. A. Goris et al. Free Rad. Res. Comm. 1987, 13–18; W. W. Zuurmond et al., Acta Anaesthesiol. Scan.) without any therapeutic result for the symptoms caused by hyperpathia and allodinia.

The therapeutic treatment with dimethyl sulfoxide proved to be efficacious only during acute CRPS.

Ketanserin is a well known synthetic drug (The Merck Index $11^{th}$ Ed., pag. 834), having formula and is a specific S2receptor antagonist with hypotensive properties, first described in EP application n°13.612.

Ketanserin has been utilised for evaluating its effect on central haemodynamics and coronary circulation [J. Cardiovasc Pharmachol 1998 Dec; 32(6):983–7]; and in the treatment of intermittent claudicatio [J. De Cree et al., Lancet 2, 775 (1984)].

L-carnitine and alkanoyl L-carnitines are well known compounds. US Pat. No. 4,255,449 and US Pat. No. 4,268,524 describe the use of L-carnitine and alkanoyl L-carnitines, respectively, for normalising abnormally high ratios of low-density lipoproteins (LDL)+very low- density lipoproteins (VLDL) to high-density lipoproteins (HDL), which constitute an etiological factor in various cardiovascular diseases. Through beta-oxidation of fatty acids, L-carnitine is capable of preventing their accumulation and of supplying the cell energy requirement (Bremner Y, TIBS 2, 207, 1977) via modulation of extra-and intra-mitochondrial CoA.

L-carnitine and particularly propionyl L-carnitine or acetyl L-carnitine can act by varying the lipid substrate from which the various vasoconstrictor and aggregation-promoting factors derive as a result of the effects of cyclo-oxygenase and lipo-oxygenase, by reducing their formation and by promoting the synthesis of antiaggregant and vasodilators factors.

Carnitine contain a single centre of asymmetry and therefore may exist as two enantiomers, designated D(+)-carnitine and L(-)carnitine-and, obviously in form of racemate. Of these only L(-)-carnitine is found in living organism, were it functions as a vehicle for transporting fatty acids across mitochondrial membranes. Moreover, L-carnitine may be in form of inner salt or in form of pharmacologically acceptable salt.

For the sake of simplicity in the following reference will be made only to L-carnitine or alkanoyl L-carnitine, it should be understood that the compositions described herein apply to L-carnitine or alkanoyl L-carnitines inner salt, or pharmacological acceptable salts thereof.

To date, the combined use of L-carnitine and ketanserin is not known for any therapeutic indication.

It has now unexpectedly been found that the co-ordinated use, a term which will be precisely defined here below, of L-carnitine or of an alkanoyl L-carnitine in which the linear or branched-chain alkanoyl has 2–6 carbon atoms, or one of their pharmacologically acceptable salts, in combination with ketanserin show a potent synergistic effect in the treatment of CRPS.

With the composition of the invention patients are able either to recover from blood circulation symptoms or from hyperpathia and allodinia symptoms.

This pharmacological activity is very important because for the first time it is possible to cure these symptoms in patients affected by CRPS.

The well known lack of toxic and side effects of L-carnitine or of the alkanoyl L-carnitines and ketanserin makes their co-ordinated use, according to the invention, particularly useful and safe for the treatment of CRPS.

In the context of the invention described herein, what is meant by "co-ordinated use" of the afore-mentioned compounds is either their co-administration, i.e. the substantially simultaneous administration of L-carnitine or one of the alkanoyl L-carnitines, or one of their pharmacologically acceptable salts, and ketanserin or, indifferently, the administration of a composition containing a combination or mixture of the aforesaid active ingredients, in addition to any excipient included.

The scope of the present invention therefore encompasses both the co-administration of L-carnitine or of an alkanoyl L-carnitine, or one of their pharmacologically acceptable salts, together with ketanserin and pharmaceutical compositions, which can be administered orally, parenterally or per intravenous infusion, containing a mixture of the two active ingredients.

In a preferred embodiment of the invention, the alkanoyl L-carnitine will be selected from the group consisting of acetyl, propionyl, butyryl, valeryl and isovaleryl L-carnitine or one of their pharmacologically acceptable salts.

What is meant by pharmacologically acceptable salt of L-carnitine or of an alkanoyl L-carnitine is any salt with an acid that does not give rise to unwanted toxic or side effects.

These acids are well known to pharmacologists and to experts in pharmacy.

Examples of pharmacologically acceptable salts of L-carnitine or alkanoyl L-carnitine, though not exclusively these, are chloride, bromide, orotate, aspartate, acid aspartate, acid citrate, acid phosphate, fumarate and acid fumarate, lactate, maleate and acid maleate, mucate, acid oxalate, acid sulphate, glucose phosphate, tartrate and acid tartrate.

One preferred composition, in unit dosage form, is a composition containing 5–100 mg of ketanserin and 500–3000 mg of L-carnitine or an equivalent amount of alkanoyl L-carnitine.

This pharmaceutical composition is useful for the treatment of symptoms related to CRPS.

Here below are given, by way of example, the pharmacological results of experimental studies aimed at providing evidence of the surprising and unexpected synergistic effect achieved with the combination of the invention.

In the following description, reference will be made only to L-carnitine, it being understood that the compositions described also apply to the above-mentioned alkanoyl L-carnitines and to the pharmacologically acceptable salts of both L-carnitine and the above-mentioned alkanoyl L-carnitines.

METHOD OF DIAGNOSIS OF CRPS

The diagnosis of chronic regional pain syndrome was made in the presence of at least five of the following symptoms:

Persistent pain at rest;
Increasing pain during exercise;
Abnormal feeling of pain like hyperpathia or allodinia;
Cold skin;
Glancing skin;
Hyperhidrosis;
Oedema;
Impaired mobility.

These symptoms were scored at the start of the treatment and after 3 months of oral treatment.

All patients gave their informed consent. Patients data are listed in the following table 1.

TABLE 1

| patient | M/F | Age (Years) | Delay (months) | Skin Temperature | Area |
|---|---|---|---|---|---|
| A | F | 37 | 13 | 28.1 | Foot |
| B | F | 38 | 6 | 29.1 | Foot |
| C | F | 39 | 3 | 33.6 | Hand |
| D | F | 40 | 30 | 31.4 | Hand |
| E | F | 24 | 3 | 28.5 | Foot |
| F | M | 48 | 108 | 25.9 | Foot |
| G | M | 37 | 192 | 23.1 | Foot |
| H | M | 42 | 6 | 29.2 | Knee |
| I | F | 55 | 6 | 33.0 | Hand |
| J | F | 50 | 3 | 31.7 | Hand |
| K | F | 36 | 16 | 25.3 | Hand |
| L | F | 42 | 9 | 32.5 | Foot |
| Mean | | 40.7 | 32.9 | | |
| S.D. | | 7.5 | 55.6 | | |

All patient had a story of surgery on the affected area of hand, foot, or knee.

In spite of the fact that this group comprised only 12 patients, they matched with the general picture of CRPS patients found in greater studies, like H. J. M. Veldman et al., The Lancet, 342, 1012–1016 (1993).

In a group of 829 CRPS patients Veldman had 76% females and 24% males. In the group treated according to the present invention, there were 67% females and 33% males.

The mean age of the Valdeman's study showed 42 years, in the study according to the example of the present invention, it was 40.7 years. Veldman found 59% CRPS of the upper extremity and 41% lower extremity.

In our group were 42% CRPS of the upper extremity and 58% CRPS of the lower extremity.

The delay time between start of the symptoms and start of the treatment was in our case of 33 months.

This extremely long time interval is the consequence of two patients with a delay of 108 and 192 months.

When we eliminate these two patients, delay time is reduced to 9.5 months, and for six patients delay time is six months or less.

Looking at the phenomenon of a warm or a cold CRPS the objective measurement of the skin temperature was used.

Taking into account that normal skin temperature is about 32° C., 7 cold extremities and five normal or warm extremities were observed.

Special attention was given to the symptom of abnormal pain feeling, hyperpathia and allodinia.

This kind of symptom was found in 6 patients.

Treatment

All i.v. treatments were performed after at least 15 minutes of acclimatisation at constant temperature (20–23° C.).

The temperature of the affected limb was recorded with Hewlett Packard electro-skin probe between digit 4 and 5. In addition continuos photoplethysmograpy of the affected hand (digit 2) or foot (digit 1), blood pressure and hearth rate were recorded.

All patients received a bolus of 10 mg of ketanserin i.v. in a running saline infusion.

Ketanserin administration was continued by rate of 4 mg per hour.

After one hour, a bolus injection of 1000 mg of L-carnitine was given.

After this infusion start, oral maintenance therapy was started is with ketanserin three times daily 20 mg, and L-carnitine three times daily 990 mg.

Results

To compare the clinical manifestation of the CRPS before and after the infusion treatment followed by three months oral therapy an evaluation of seven symptoms was made.

The seven symptoms were: pain at rest, pain during exercise, impaired mobility, hyperhidrosis, oedema, small veins and allodinia/ hyperpathia.

A scale with five degree was used. The nurse recorded the degree of the symptoms of the patient according to the following scale: absent, mild, reasonable, moderate and severe.

Figure 1:
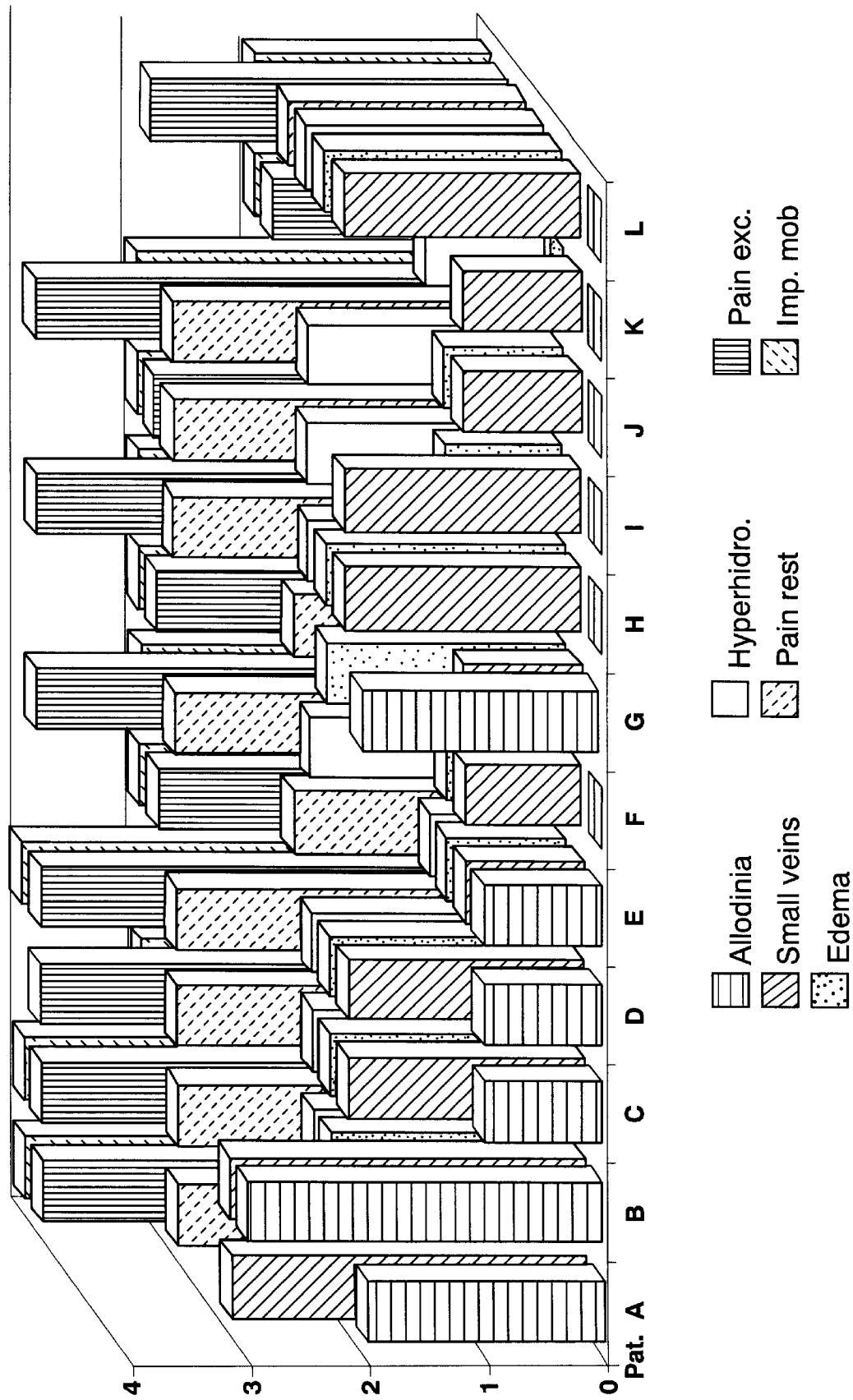
FIG. 1 shows the inventorisation at starting time; special attention was given to the symptom allodinia, which is pointed on the first line.

This symptom was present in six out of these twelve patients. The results after three months are shown in FIG. 2.

After the intravenous treatment with ketanserin all patients had peripheral circulation of the affected limb normalised, as proven in the past by Moesker (above cited) and by M. H. Hanna et al. [Pain, 38, 145–150 (1989)].

The symptom of small vein disappeared and the skin temperature was normalised.

After three months treatment with the two compounds according to the invention, patient "F" which was a severe case with a delay time of 108 months, had still the worst symptomatology, with pain at rest, pain during exercise and impaired mobility.

Patient "C" was a remarkably case, who had good recovery, but still oedema and Hyperhidrosis.

Patient "B" was fully cured of any complaint of CRPS, despite she had a three months old full blow CRPS, with a skin temperature of 29,1° C. and seriously debilitating allodinia of the affected foot. Is noteworthy that the allodinia symptom disappeared in all patients that showed this symptom.

Impaired mobility and pain during exercise did not disappear completely probably because the treatment time with the combination according to the present invention was too short.

Other positive results were obtained changing the therapeutic treatment protocol above cited.

In fact, it is possible to increase or decrease the amount of the two compounds either during the initial intravenous infusion or during the maintenance therapeutic treatment (os).

In mild or recent CRPS it is possible to start directly with the above cited maintenance therapeutic treatment (os) with ketanserin and L-carnitine, three times daily.

It is an object of the present invention an orally or parenterally administrable composition comprising ketanserin and L-carnitine or an alkanoyl L-carnitine or one of its pharmacologically acceptable salts.

Object of the present invention is also the co-ordinated use of the above-mentioned compounds i.e. the substantially simultaneous administration of L-carnitine or one of the alkanoyl L-carnitines, or one of their pharmacologically acceptable salts, and ketanserin or, indifferently, the administration of a composition containing a combination or mixture of the aforesaid active ingredients, in addition to any excipient included.

The composition of the invention can be orally, parenterally or intravenously per infusion administered. The composition according to the invention can be in the form of tablets, capsules, effervescent sachets, suppositories or vials.

Further object of the present invention is to provide a therapeutical kit comprising in the same package:

a) a first set of vials for intravenous infusion, said first set of vials comprising 5–50 mg of ketanserin in admixture with pharmacologically acceptable vehicle and/or excipient, a second set of vials for intravenous infusion, said second set of vials comprising 500–2000 mg of L-carnitine or an equivalent amount of an alkanoyl L-carnitine or one pharmacologically acceptable salts pharmaceutical composition comprising 100–3000 thereof, in admixture with pharmacologically acceptable vehicle and/or excipient;

and further comprising in the same package, b) a first orally administrable pharmaceutical composition comprising 5–100 mg of Ketanserin and a second orally administrable mg of L-carnitine or of an alkanoyl L-carnitine or one pharmacologically acceptable salts thereof, in admixture with pharmacologically acceptable vehicle and/or excipient.

What is claimed is:

1. A combination consisting synergistic effective amounts of ketanserin and L-carnitine or a pharmacologically acceptable salt thereof.

2. Pharmaceutical composition comprising synergistic effective amounts of active ingredients ketanserin and L-carnitine or a pharmacologically acceptable salt thereof, in admixture with pharmacologically acceptable vehicle and/or excipient.

3. The composition according to claim 2, for oral, parenteral or intravenous infusion administration.

4. The composition according to claim 2, wherein the pharmacologically acceptable salt of L-carnitine is selected from the group consisting of chloride, bromide, orotate, aspartate, acid aspartate, acid citrate, acid phosphate, fumarate and acid fumarate, lactate, maleate and acid maleate, mucate, acid oxalate, acid sulphate, glucose phosphate, tartrate and acid tartrate.

5. The composition according to claim 2, in unit dosage form, comprising 5–100 mg of Ketanserin and 100–3000 mg of L-carnitine.

6. The composition according to claim 5, suitable for oral administration.

7. A kit comprising synergistic effective amounts in the same package a first set of vials for intravenous infusion, said first set of vials comprising 5–50 mg of ketanserin in admixture with pharmacologically acceptable vehicle and/or excipient, a second set of vials for intravenous infusion, said second set of vials comprising 500–2000 mg of L-carnitine one pharmacologically acceptable salts thereof, in admixture with pharmacologically acceptable vehicle and/or excipient.

8. A kit comprising synergistic effective amounts in the same package a first orally administrable pharmaceutical composition comprising 5–100 mg of Ketanserin and a second orally administrable pharmaceutical composition comprising 100–3000 mg of L-carnitine.

9. A method of treating chronic regional pain syndrome comprising the coordinated administration of synergistic effective amounts of ketanserin and L-carnitine or a pharmacologically acceptable salt thereof to a patient suffering from said syndrome.

10. The method of claim 9, wherein the pharmacologically acceptable salt of L-carnitine is selected from the group consisting of chloride, bromide, orotate, aspartate, acid aspartate, acid citrate, acid phosphate, fumarate and acid fumarate, lactate, maleate and acid maleate, mucate, acid oxalate, acid sulphate, glucose phosphate, tartrate and acid tartrate.

11. The method of claim 9, wherein there is administered 5–100 mg of ketanserin and 100–3000 mg of L-carnitine, in a single unit dosage form.

12. The method of claim 9, wherein there is administered 5–100 mg of ketanserin in a first unit dosage form and 100–30000 mg of L-carnitine in a second unit dosage form, said first and second unit dosage forms being physically separated.

* * * * *